United States Patent [19]

Hansen et al.

[11] 4,183,849
[45] Jan. 15, 1980

[54] THERAPEUTIC INSULIN PREPARATION AND A PROCESS FOR THE PRODUCTION OF A STABLE INSULIN PREPARATION WITH PROTRACTED EFFECT

[75] Inventors: Bruno A. Hansen, Rodovre; Finn H. Andresen, Hillerod, both of Denmark

[73] Assignee: Nordisk Insulinlaboratorium, Gentofte, Denmark

[21] Appl. No.: 858,916

[22] Filed: Dec. 8, 1977

Related U.S. Application Data

[63] Continuation-in-part of Ser. No. 648,218, Jan. 12, 1976, abandoned.

[30] Foreign Application Priority Data

Jan. 15, 1975 [DK] Denmark ............................ 83/75

[51] Int. Cl.² ............................................. A61K 37/26
[52] U.S. Cl. ................................. 260/112.7; 424/178
[58] Field of Search ....................... 260/112.7; 424/178

[56] References Cited

U.S. PATENT DOCUMENTS

| 2,704,737 | 3/1955 | Bischoff | 424/178 |
| 3,060,093 | 10/1962 | Poulsen et al. | 424/178 |
| 3,868,358 | 2/1975 | Jackson | 260/112.7 |
| 3,907,676 | 9/1975 | Jorgensen | 260/112.7 |

FOREIGN PATENT DOCUMENTS

737961 10/1955 United Kingdom .................. 260/112.7

Primary Examiner—Frederick E. Waddell
Attorney, Agent, or Firm—Ladas, Parry, Von Gehr, Goldsmith & Deschamps

[57] ABSTRACT

Novel stable insulin preparations with protracted action and reduced or no antigenicity are obtained by reacting insulin free of antigenic impurities with an organic compound having basic amino groups, preferably a basic polypeptide or a cleavage product of a basic polypeptide, such as protamine, in a buffered protein dissociating or protein depolymerizing aqueous medium. Examples of preferred protein dissociating or protein depolymerizing media are aqueous solutions containing urea, a lower alkanol dialkylformamide, acetamide, N-alkylacetamide or acetonitrile.

17 Claims, 6 Drawing Figures

Figure 2:
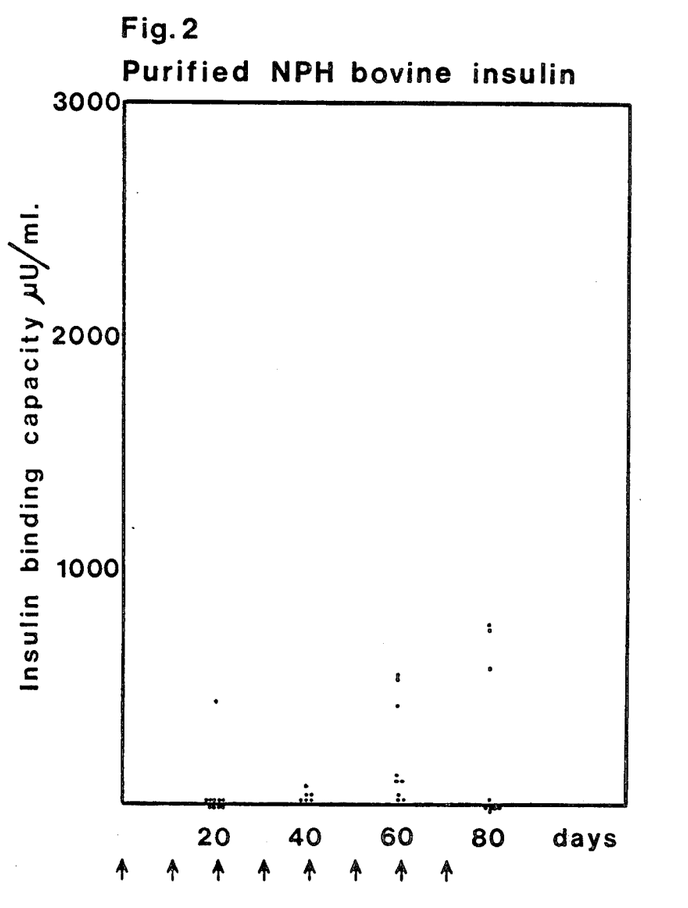

Fig. 2
Purified NPH bovine insulin

THERAPEUTIC INSULIN PREPARATION AND A PROCESS FOR THE PRODUCTION OF A STABLE INSULIN PREPARATION WITH PROTRACTED EFFECT

This application is a continuation-in-part of the application entitled A Therapeutic Insulin Preparation and a Process for the Production of a Stable Insulin Preparation with Protracted Effect, Ser. No. 648,218 filed by the applicants herein on Jan. 12, 1976 now abandoned.

This invention relates to a process for producing a stable insulin preparation with protracted effect and reduced or no antigenicity by reacting insulin with an organic base containing amino groups.

In the treatment of diabetes mellitus insulin preparations derived from porcine or bovine pancreas are generally used. Thus, approximately 30% of the world consumption of insulin is based on porcine insulin and approximately 70% on bovine insulin. Insulin from other animals has been suggested, for example sheep insulin, but so far it has not attained any major commercial significance.

Insulin therapy previously involved several inconveniences which manifested themselves inter alia as allergy and lipodystrophy.

For many years it has also been known that the conventional insulin treatment for most patients resulted in the formation of insulin antibodies, which might lead to increased insulin requirements, in that unknown amounts of insulin may be bound to the antibodies and thus rendered inactive as a regulator of the blood sugar.

The primary cause of the antibody formation and the consequent high insulin consumption was long supposed to be the presence of various impurities in normal commercial insulin. However, it was also supposed that pure insulin was antigenic. Thus, as early as in 1964 Mr. T. Deckert suggested in his doctoral thesis "Insulin Antibodies" that the insulin molecule itself shows some antigenicity, and that this is intensified by the presence of certain impurities.

On the basis of this theory the person skilled in the art would expect that the problem of antigenicity could not be solved definitely by subjecting the insulin to a thorough purification.

The amount of impurities in recrystallized insulin is typically in the range from 5–10% or more. As examples of such impurities may be mentioned insulin dimer, proinsulin, intermediary insulin (the stage between proinsulin and insulin), arginine insulin, ethylester insulin, mono-desamido insulin and didesamido insulin. The first three of these compounds are known to be highly antigenic. It is also known that the fourth or the fifth or both of these are highly antigenic, while the sixth and the seventh compound are not or only slightly antigenic.

It is known to remove the said impurities by gel filtration and/or ion exchange chromatography, whereby it is possible to obtain a highly purified insulin containing substantially only a single component. Thus, in "The Chromatography of Insulin in Urea-containing Buffer," J. Biol. Chem. 235 (1960), p. 2294–2299, R. David Cole has described highly purified insulin preparations and a process to prepare such by ion exchange chromatography using urea-containing buffer solutions as eluents.

The preparations are so thoroughly purified by this process that they can be considered as containing only one component.

The heterogenicity of different insulin products including commercial crystalline or recrystallized insulin has been examined by for example J. Arthur Mirsky and Kazunori Kawamura, cf. "Heterogeneity of Crystalline Insulin," Endocrinology 78, (1966), p. 1115–1119, who separated insulin from many various animal species, and also human insulin, and isolated the individual insulin components by gel filtration and separation by polyacrylamide gel celectrophoresis (DISC PAGE).

Attempts have been made to prepare low antigenic or antigen free insulin preparations on the basis of such monocomponent or single component insulin products. Thus, British patent specification No. 1,285,023 relates to an injectable insulin preparation containing insulin being free of proteins of pancreatic origin with a molecular weight above 6000 and showing essentially a single component when a solution thereof is analyzed by polyacrylamide gel electrophoresis (DISC PAGE).

Though the above patent was published several years ago, and in spite of the fact that even before this publication (cf. the above-mentioned work from 1960 by Cole) it was possible to prepare single component insulin, insulin preparations on the basis of single component bovine insulin have till now not attained any commercial significance.

On the other hand, preparations on the basis of single component porcine insulin are commercially available, but they are not antigen free.

The antigenicity of monocomponent or single component insulin has been examined by R. E. Chance et al: "The immunogenicity of insulin preparations," Acta Endocrinologica Supplementum 205, Copenhagen 1976. The result of these examinations is that preparations based on single component bovine insulin show practically the same antigenicity as preparations containing commercial recrystallized insulin.

Preparations based on single component porcine insulin had lower antigenicity than the corresponding commercial preparations based on recrystallized porcine insulin, but still a considerable residual antigenicity.

Several examinations indicate that the physical state of insulin plays an important role for the formation of antibodies. (Kumar et al: Horn. Metab. Res. 6, (1974) 175–177, and P. A. Piers et al: Neth J. Med. 17 (1974) p. 234–238).

It is an object of the present invention to prepare a stable insulin preparation with protracted action and reduced or no antigenicity.

A specific object of the invention is to prepare an insulin preparation with protracted action and reduced or no antigenicity on the basis of purified or highly purified bovine insulin.

The present invention is based on our new recognition that both purified and highly purified insulin, especially bovine insulin, form aggregates or polymers which may cause antigenicity, and that it is possible to prevent formation of aggregates and to fix the insulin in a stabilized form with reduced or no antigenicity.

This is achieved by the process of the invention whereby purified or highly purified insulin is reacted with an organic base comprising amino groups, the reaction being conducted in an aqueous buffered protein dissociating or protein depolymerizing medium which will maintain the insulin in a dissolved and stabilized monomeric or loosely aggregated form during the reaction, until the reaction is completed.

By the expression "loosely aggregated form" is understood a form where the insulin may reversibly be converted into monomeric form, the equilibrium being displaced towards monomeric form during the reaction when said reaction takes place in the protein dissociating or protein depolymerizing medium. On the other hand, there must be no irreversibly aggregated or polymerized insulin, such as dimer insulin.

By the process according to the invention it is achieved that the insulin molecules in monomeric form reacts with the organic base comprising amino groups and thereby are fixed in stabilized monomeric state.

It is universally known to prepare insulin preparations with protracted action by reacting insulin and a base, such as protamine. Though highly purified insulin has been used for the preparation of such preparations, such insulin has been a crystallized and redissolved insulin which has therefore been more or less irreversibly aggregated or polymerized, or the reaction has been carried out under conditions where a minor or major amount of the insulin molecules aggregates or polymerizes irreversibly before they are fixed by reaction with protamine or a similar base.

The process according to the invention uses insulin which previously has been freed of irreversibly aggregated or polymerized insulin, and the reaction is carried out under conditions where such an irreversible aggregation or polymerization does not take place because of the presence of the protein dissociating or protein depolymerizing medium. The antigenic impurities have preferably also previously been removed from the insulin. However, it is not necessary to remove all impurities. Thus, impurities not being substantially antigenic are permissible, such as mono-desamido insulin and didesamido insulin. Insulin preparations containing such impurities cannot be considered to be highly purified, but may nevertheless be stabilized to form injectable insulin preparations with protracted action with reduced or no antigenicity by reaction with protamine under the conditions set forth according to the invention.

Examples of suitable organic bases applicable in the process according to the invention are polypeptides, for example polyarginine, somatostatine, protamine or cleavage products thereof or globine. An example of an applicable base which is not a polypeptide is surfene, that is 1,3-bis-(4-amino-2-methyl-6-quinolyl)urea.

According to the invention the reaction is expediently performed in the presence of urea as a stabilizer. Examples of other suitable stabilizers are lower alkanols, such as methanol and ethanol, dialkylformamides, for example dimethylformamide, acetamide, N-alkyl-acetamides, such as N-methylacetamide, and acetonitrile. These stabilizers have a protein dissociating or protein depolymerizing effect and are therefore effective in stabilizing the insulin in a monomeric or loosely aggregated form.

The invention can also be used in connection with insulin from many different animal species, such as swine, ox or sheep, but the invention is especially important in connection with bovine insulin. Instead synthetic insulin may be used, for example synthetic human insulin, or insulin derivatives or analogues.

In all cases all antigenic impurities are removed as much as is possible or desired prior to the reaction with the protamine. This purification may be performed in a manner known per se, such as by recrystallization and/or gel filtration and/or ion exchange chromatography. The insulin thus purified is maintained, as stated, in a stabilized monomeric or loosely aggregated form during the reaction. Hereby the polymerization or formation of aggregates is avoided which might otherwise occur in the absence of the stabilizing medium, such as by intermediary isolation and resolution of the purified or highly purified insulin. After the reaction with protamine the insulin is fixed in stabilized monomeric form and will not be able to form antigenic polymerizates or aggregates, even though the stabilizing medium is removed and the insulin-protamine-complex is suspended in a known carrier medium for injection.

A preferred embodiment of the invention is specific in that an insulin-containing fraction obtained by chromatographic purification of insulin by means of a buffered protein dissociating or protein depolymerizing aqueous eluent, is mixed with an aqueous solution of an organic base comprising amino groups, whereupon the produced insulin preparation is isolated. This procedure provides effective security against aggregation in that the highly purified insulin is not first isolated as such with a consequent risk of aggregation. Besides, the said process is very simple, for directly combined with an effective purification the protracted action insulin is precipitated in stable form.

The chromatographic purification can be carried out in a manner known per se as an arbitrary, suitable ion exchange resin is used. Examples of this are Amberlite® IRC-50, DEAE® cellulose, Amberlite® CG-50 type II or DEAE Sephadex® A-25. A strong alkaline anion exchange resin is preferred as an effective fractioning is achieved thereby.

It is expedient to conduct the reaction between the insulin and the organic base containing amino groups in an aqueous buffer solution containing dissolved urea in a concentration of at least 2 molar, such as 5–8 molar, whereupon the reaction product is precipitated by diluting the reaction product. A suitable stabilization can be obtained by using a buffer being approximately 7 molar as regards urea.

After the precipitation of the insulin protamine complex said complex can be suspended in a known carrier medium to obtain an injectable preparation with protracted action.

The insulin protamine preparation can also be isolated or recovered in another way. If a protein dissociating or protein depolymerizing solvent is used as a medium said solvent can be replaced by the desired carrier medium by decanting, filtration or centrifuging and resuspension of the preparation in the medium. If the medium contains a volatile solvent, such as methanol or ethanol, said solvent can be removed by vacuum evaporation before or after the adding of the carrier medium.

Another embodiment of the process according to the invention comprises the steps of subjecting insulin to ion chromatographic purification using an aqueous buffered solution containing 50–70% lower alkanol as an eluent, isolating a fraction containing highly purified insulin, admixing a buffered solution of protamine to said fraction, removing the lower alkanol and isolating the stabilized insulin protamine complex containing preparation.

Methanol and ethanol are the preferred components of the medium of this embodiment. Thus, an approximately 60% aqueous ethanol solution can be used with advantage as an eluent. The chromatography can be performed with an arbitrary ion exchange resin, however, a strong alkaline anion exchange resin is preferred, such as Dowex® 1-X2 or QAE-Sephadex® A-25. To ensure complete removal of impurities having a molecular weight above 6000 insulin having been presubjected to gel filtration, for example on Sephadex G-50 can be used as a starting material for the ion chromatography.

The process according to the invention will be illustrated in greater detail below by way of examples.

EXAMPLE 1

250 mg of recrystallized bovine insulin was dissolved in 5.2 ml of stabilized buffer solution consisting of 7 M (molar) deionized urea and 0.02 M tris having a pH of 8.1. The solution was mixed with 5.2 ml of 7 M urea. The pH of the mixture was adjusted to 8.1. A column of a diameter of 5 cm$^\phi$ was packed with a layer 2.1 cm high DEAE cellulose (Whatmann DE 52) and equilibrated with a buffer solution of the above composition. The insulin solution was introduced in the column and elution performed at a rate of 75 ml per hour according to the following schedule:

2.5 hours with a buffer of the composition defined above,
3 hours with a buffer of the composition defined above to which had been added 0.0045 mole of sodium chloride per liter,
12 hours with a buffer of the composition defined above to which had been added 0.011 mole of sodium chloride per liter.

The eluate was divided into fractions. The highly purified fractions were collected and the content of the insulin determined. In a 7 M urea solution of the same volume as the mixture of the highly purified fractions protamine was dissolved in the amount necessary for obtaining the isophanic ratio of highly purified insulin to protamine.

The insulin solution was added slowly and dropwise to the protamine solution while stirring and, possibly after dilution to a urea concentration of 1 M, a protamine-insulin complex in amorphous state will be precipitated.

The precipitate was isolated by centrifuging and presented substantially only one band when 300 μg was subjected to isoelectric focusing in polyacrylamide gel and using 2% of ampholine ® (pH3–10) in 6 M deionized urea.

This precipitate can be used for the production of injectable insulin preparations by suspension in known carrier media.

EXAMPLE 2

A stabilized buffer solution was prepared by mixing two solutions, I and II, in a ratio to make pH=6.0.

Solution I comprises 7 molar deionized urea and 0.13 molar sodiumdihydrogenphosphate.

Solution II comprises 7 molar deionized urea and 0.13 molar disodiumhydrogenphosphate.

400 mg recrystallized bovine insulin was dissolved in 3 ml of this buffer, and the pH was subsequently adjusted to 6.0 with a small amount of solution II, whereafter the resultant mixture was filtered.

A column of a diameter of 2.5 cm was packed with a 27 cm layer of amberlite resin CG-50 type II and equilibrated with a buffer solution of the above composition. The insulin solution was introduced in the column, which was eluted at a rate of 40 ml per hour with a buffer solution of the above composition.

The eluate was divided into fractions. The purified insulin fractions were collected and the content of insulin determined. In a 7 molar urea solution of the same volume as the mixture of purified fractions protamine was dissolved in the amount necessary for obtaining the isophanic ratio of the purified insulin to the protamine.

The insulin solution was added slowly to the protamine solution while stirring, and, possibly after dilution to a urea concentration of 1 molar, a protamine-insulin complex was precipitated in amorphous state.

The precipitate was isolated by centrifuging and exhibited the same purity as the product described in Example 1.

The precipitate can be used for the production of injectable insulin preparations by suspension in known carriers.

EXAMPLE 3

The procedure of Example 1 or 2 was repeated and in the protamine solution was introduced zinc chloride corresponding to 0.5% Zn ions calculated on the amount of insulin and 0.3% m-cresol based on the volume of the mixture. The pH of the mixture was maintained within the range of 6–9, with the result that the protamine-insulin complex was precipitated in crystalline state.

The precipitate was isolated by centrifuging and presented substantially only one band when 300 μg was subjected to isoelectric focusing in polyacrylamide gel using 2% of ampholine (pH 3–10) in 6 M deionized urea.

The precipitate can be used for the production of injectable insulin preparations by suspension in known carriers.

EXAMPLE 4

The procedure of Example 1 or 2 was repeated, but as starting material was used recrystallized bovine insulin purified gel filtration on Sephadex G-50.

The prepared product was of the same purity as the product described in Example 1.

EXAMPLE 5

The procedure of Example 1 or 2 was repeated using porcine insulin instead of bovine insulin.

The derived protamine-porcine insulin complex was as pure as the complex prepared in Example 1.

EXAMPLE 6

The procedure of Example 1 or 2 was repeated using as starting material porcine insulin prepared by salting-out an aqueous crude extract formed in the production of insulin by addition of NaCl to 3.5 M at pH 8.5. The obtained salt cake was desalted in conventional manner prior to the ion exchange.

The prepared product was of the same purity as the product described in Example 1.

EXAMPLE 7

The procedure of Example 6 was repeated and the obtained salt cake was subjected to gel filtration on Sephadex G-50.

The product was of the same purity as the product described in Example 1.

EXAMPLE 8

The procedure of Example 1 or 2 was repeated substituting poly-L-arginine (degree of polymerization 296) for protamine.

EXAMPLE 9

The procedure of Example 1 or 2 was repeated, but to the pooled purified insulin fractions was added a 0.2% aqueous solution of bis-(4-amino-2-methyl-quinolyl-6-)urea-hydrochloride in an amount equivalent to 10% by weight of the insulin amount present in said fractions. Thereby, possibly after dilution to a urea concentration of 1 M with 0.025 M sodium phosphate buffer, pH 7.3, an insulin complex was precipitated, which was left to stand for some time and then isolated by centrifuging.

The prepared product was of the same purity as the product described in Example 1.

EXAMPLE 10

The procedure of Example 9 was repeated using as starting material recrystallized bovine insulin purified by gel filtration on Sephadex G-50. The prepared product was of the same purity as the product described in Example 1.

EXAMPLE 11

The procedures of Example 9 were repeated using porcine insulin instead of bovine insulin.

The derived porcine insulin complex was as pure as the complex prepared in Example 1.

EXAMPLE 12

The procedure of Example 9 was repeated using as starting material porcine insulin produced by salting-out an aqueous crude extract formed in the production of insulin by addition of salt to obtain 3.5 M at pH 8.5. The obtained salt cake was desalted in conventional manner prior to the ion exchange. The prepared product was of the same purity as the product described in Example 1.

EXAMPLE 13

The procedure of Example 12 was repeated and the obtained salt cake was subjected to gel filtration on Sephadex G-50.

The product was of the same purity as the product described in Example 1.

EXAMPLE 14

A column of 2.6×80 cm was packed with DEAE-Sephadex A-25 which was previously swelled and equilibrated in a buffer consisting of 0.15 M ammonium hydroxide in 7 M dimethylformamide adjusted to a pH of 9.0 with 5 N hydrochloric acid. 300 mg bovine insulin purified gel filtration on Sephadex G-50 were dissolved in 40 ml of the above buffer and introduced in the column, whereupon an elution was performed for 2 hours with the above puffer at a rate of 200 ml per hour. Then the elution was continued, and at the same rate a linear gradient was impressed, said gradient being produced from 2700 ml of the above buffer and 2700 ml buffer consisting of 0.25 M ammonium hydroxide in 7 M dimethylformamide adjusted to pH=9.0 with 5 N hydrochloric acid.

The eluate was divided into fractions. The highly purified fractions were collected, and the insulin content was determined. The pH was adjusted to 7.9 with 5 N hydrochloric acid, and m-cresol was added until the solution contained 0.2% of said m-cresol. When the total zinc content of the solution had been adjusted to 0.5% by weight of the insulin content, the amount of protamine sulphate necessary to obtain the isophanic ratio was added in the form of a 1% aqueous solution, and the mixture was stirred carefully. After a standing period of 15 minutes at 20° C. 6 volume 1/75 sodium phosphate buffer was added, pH=7.3, containing 0.2% m-cresol, and after a short stirring it was left to stand at 20° C. for 16 hours. Hereby the amorphously precipitated protamine-insulin-complex was crystallized.

By replacing the above liquid by a known carrier medium the precipitate was converted into an injectable insulin preparation.

When a precipitate of 300 μg was isoelectrically focussed in polyacrylamide gel using 2% ampholine (pH=3-10) in 6 M deionized urea, said precipitate showed essentially only one band.

EXAMPLE 15

A column with a diameter of 2.6 cm and a height of 4.4 cm was packed with QAE-Sephadex A-25 which was previously swelled and equilibrated in a buffer consisting of 0.1 M tris-(hydroxymethyl-amino methane in 60 vol.% ethanol adjusted to pH=7.35 with 5 N hydrochloride acid.

250 mg bovine insulin, which had been purified by gel filtration on Sephadex G-50, were dissolved in 10 ml 0.1 M tris in 60% ethanol adjusted to pH=8.5 with hydrochloric acid, and after filtering the solution was introduced in the column. Then the column was eluted with the equilibrium buffer at a rate of 10 ml per hour. The eluate was divided into fractions, the highly purified fractions were collected, and the insulin content was determined. Then m-cresol was added until the solution contained 0.2% of said m-cresol, whereupon the total zinc content was adjusted to 0.5% by weight of the insulin content. Then the amount of protamine sulphate necessary to obtain the isophanic ratio was added in the form of a 1% aqueous solution, and the mixture was stirred carefully. After a standing period of 15 minutes at 20° C. 9 volume 1/75 sodium phosphate buffer was added, pH=7.3, containing 0.2% m-cresol, and after a short stirring it was left to stand at 20° C. for 16 hours. Hereby the amorphously precipitated protamine-insulin-complex was crystallized.

By replacing the above liquid by a known carrier medium the precipitate was converted into an injectable insulin preparation.

When a precipitate of 300 μg was isoelectrically focussed in polyacrylamide gel using 2% ampholine (pH=3-10) in 6 M deionized urea, said precipitate showed essentially only one band.

EXAMPLE 16

In a refrigerated room at 5° C. a column with a diameter of 2.6 cm and a height of 11 cm was packed with QAE Sephadex A-25 which was previously swelled and equilibrated in a buffer consisting of 0.5 M tris-(hydroxymethyl)-amino methane in 8 M acetamide ajusted to pH=8.0 with glacial acetic acid.

300 mg bovine insulin, which had been purified by gel filtration on Sephadex G 50, were dissolved in 30 ml of the above buffer and introduced in the column, whereupon an elution was performed for one hour at a rate of 80 ml per hour. Then the elution was continued, and at the same rate a linear gradient was impressed, said gradient being prepared from 2000 ml of the above buffer and 2000 ml of the same buffer containing furthermore 0.15 M sodium chloride.

The eluate was divided into fractions. The highly purified fractions were collected and the insulin content was determined. After admixture of m-cresol until a content of 0.2% was obtained, the total zinc content of the solution was adjusted to 0.5% by weight of the insulin content with an 0.15 M zinc chloride solution, and then the amount of protamine sulphate necessary to obtain the isophanic ratio was added in the form of a 1% aqueous solution. The mixture was stirred carefully, and after a standing period of 15 minutes 7 volume 1/75 M sodium phosphate buffer was added, pH=7.3, containing 0.2% m-cresol, whereupon it was left to stand for another 16 hours at 20° C. Hereby the amorphously precipitated protamine-insulin-complex was crystallized.

By replacing the above liquid by a known carrier medium the precipitate was converted into an injectable insulin preparation.

When a precipitate of 300 μg was isoelectrically focussed in polyacrylamide using a 2% ampholine (pH=3-10) in 6 M deionized urea, said precipitate showed essentially only one band.

EXAMPLE 17

In a refrigerated room at 5° C. a column with a diameter of 2.6 cm and a height of 12 cm was packed with QAE Sephadex A-25 which was previously swelled and equilibrated in a buffer consisting of 0.05 M tris-(hydroxymethyl)-amino methane in 7 M acetonitrile adjusted to pH=8.2 with 5 N hydrochloric acid.

300 mg bovine insulin, which had been purified by gel filtration on Sephadex G-50, were dissolved in 30 ml of the above buffer, the pH being adjusted to 9.3 with 2 N NaOH and then to 8.2 with 2 N hydrochloric acid and introduced in the column, whereupon an elution was performed for one hour with the above buffer at a rate of 75 ml per hour. Then the elution was continued, and at the same rate a linear gradient was impressed, said gradient being produced from 1800 ml of the above buffer, and 1800 ml of the same buffer containing furthermore 0.15 M sodium chloride.

The eluate was divided into fractions. The highly purified fractions were collected, and the insulin content was determined. After admixture of m-cresol until a content of 0.2% was obtained, the total zinc content of the solution was adjusted to 0.5% by weight of the insulin content with an 0.15 M zinc chloride solution, and then the amount of protamine sulphate necessary to obtain the isophanic ratio was added in the form of a 1% aqueous solution. The mixture was stirred carefully, and after a standing period of 15 minutes 6 volume 1/75 M sodium phosphate buffer was added, pH=7.3, containing 0.2% m-cresol, whereupon it was left to stand for another 16 hours at 20° C. Hereby the amorphously precipitated protamine-insulin-complex was crystallized.

By replacing the above liquid by a known carrier medium the product was converted into an injectable insulin preparation.

When a precipitate of 300 μg was isoelectrically focussed in polyacrylamide gel using 2% ampholine (pH=3-10) in 6 M deionized urea, said precipitate showed essentially only one band.

EXAMPLE 18

Example 16 was repeated, however, the buffer now consisted of 0.05 M tris-(hydroxymethyl)-amino methane in 5 M aqueous N-methylacetamide adjusted to pH=8.2 with 5 N hydrochloric acid, and only 4 volume phosphate buffer were admixed the insulin solution at the crystallization.

EXAMPLE 19

The procedure of Example 17 was repeated, the collected highly purified insulin fractions being introduced in a column packed with Sephadex G-25 which was swelled in a medium consisting of 1/60 M disodium-mono-hydrogen-phosphate in 1 M acetamide pH 7.65, so that the volume introduced did not exceed 20% of the total volume of the column. The column was then eluted with the above medium at a rate of 20 ml per hour per cm$^2$, and the insulin containing eluate fractions were collected. After determination of the insulin content the total zinc content of the solution was adjusted to 0.5% by weight of the insulin content with 0.15 M zinc chloride in 1 M acetamide, and then were added ¼ volume 1/100 M hydrochloric acid containing 1.5% m-cresol, and the amount of protamine sulphate necessary to obtain the isophanic ratio. Having been left to stand for 16 hours at 20° C. the precipitated protamine-insulin-complex was crystallized. The product obtained thereby was of the same purity as the product described in Example 17.

By replacing the above liquid by a known carrier medium the precipitate can be used to prepare injectable insulin preparations.

To illustrate the changed immunogenic properties of the protamine-insulin-complex isolated according to the invention comparative tests have been conducted on rabbits, which are the animals normally used for examination of the antigenic properties of insulin and insulin-like components.

In the comparative tests the following preparations were used:

1. *Conventional NPH bovine insulin* prepared in conventional manner from recrystallized bovine insulin containing the impurities mentioned in the specification.
2. *Purified NPH bovine insulin* prepared in conventional manner from purified crystalline bovine insulin but freed of the impurities mentioned in the specification by column chromatography.
3. Purified NPH bovine insulin prepared according to the invention as described in Example 3, *New NPH Bovine Insulin.*

The rabbits were injected subcutaneously every 10th day with a constant dose of 20 i.u. of the insulin preparation to be tested. It was not possible to show any essential antibody formation after the injection of conventional NPH bovine insulin without adjuvants, and with a view to comparison it was therefore necessary to adopt an immunization procedure normally used in the preparation of antibodies, that is to inject the insulin preparations of the 1st injection emulsified in Freund's Complete Adjuvant and in subsequent injections emulsified in Freund's Incomplete Adjuvant.

The insulin antibody formation was examined at intervals of 20 days using the method described by Ortved-Andersen et al. (Acta Endocr. (Kbh.) 69, 195–208, 1972).

Figure 1:
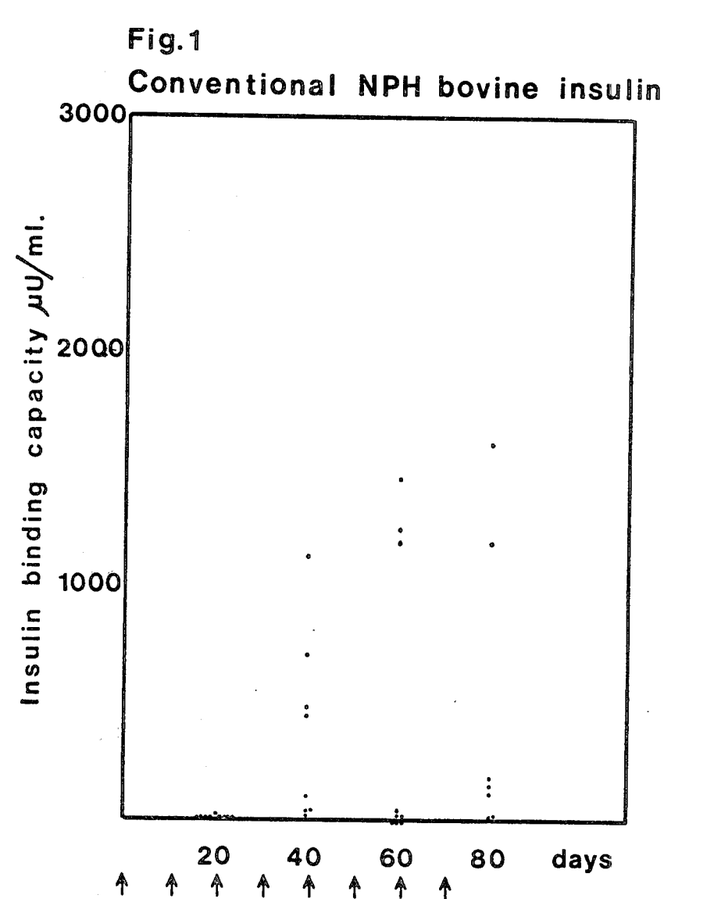
Figure 3:
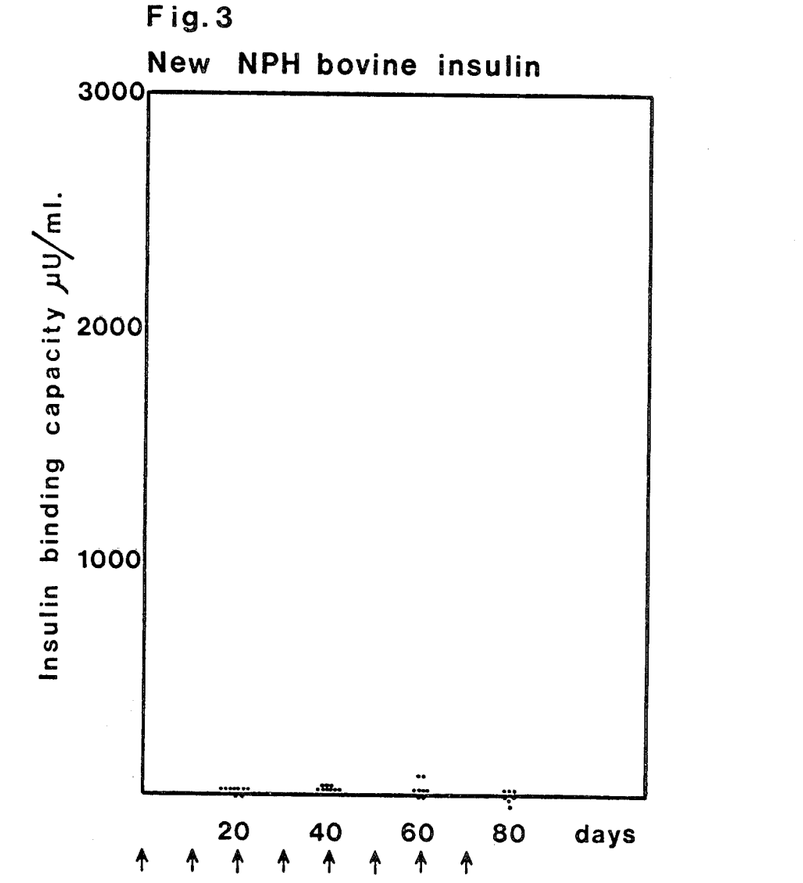

The obtained results are illustrated in FIGS. 1, 2 and 3.

It will be seen from the results that it was possible to show formation of antibody to conventional NPH bovine insulin and reduced formation of antibody to purified NPH bovine insulin, whereas it was practically impossible to show any formation of antibody to the new NPH bovine insulin prepared according to the invention. It should be noted that preparations 2 and 3 were purified by the same chromatography purification, the only difference being that preparation 2 was prepared by first isolating the insulin and then reacting it with protamine in known manner, whereas preparation 3 was prepared by conducting the reaction in a urea-containing eluate without prior isolation of the insulin.

A further series of tests were made using a milder immunization procedure from which the initial stimulation of the immunity instrument with killed bacteria had been excluded, i.e. the injected preparations were in all cases emulsified in Freund's Incomplete Adjuvant. The rabbits were injected every 10th day with a constant dose of 20 i.u.

The insulin antibody formation was examined at intervals of 10 days using a newly developed method described below.

Figure 4:
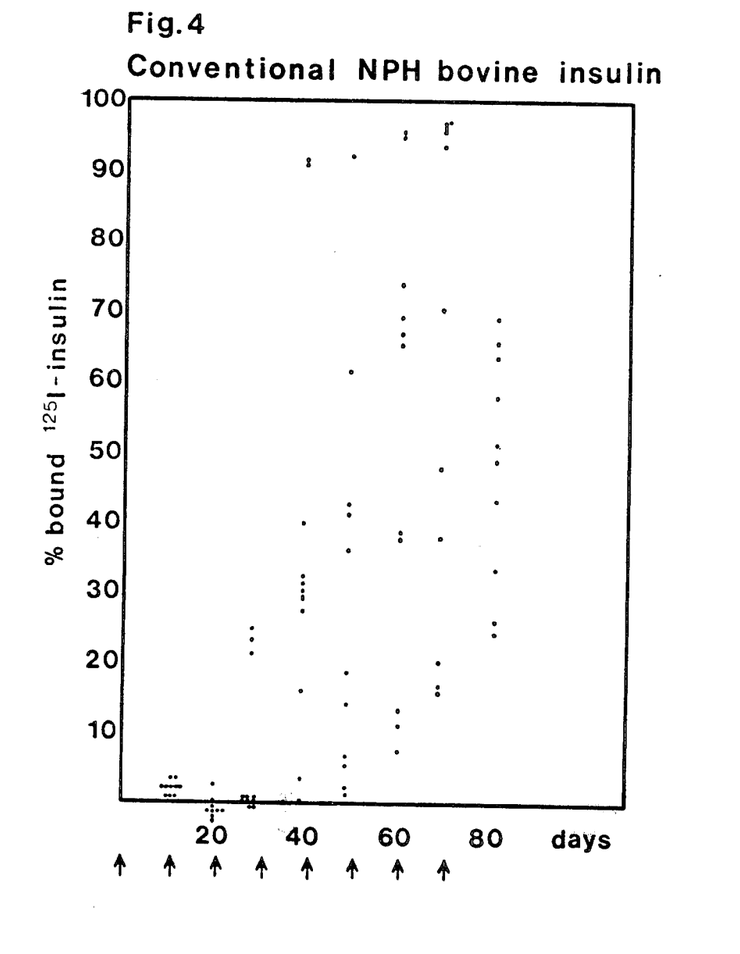
Figure 5:
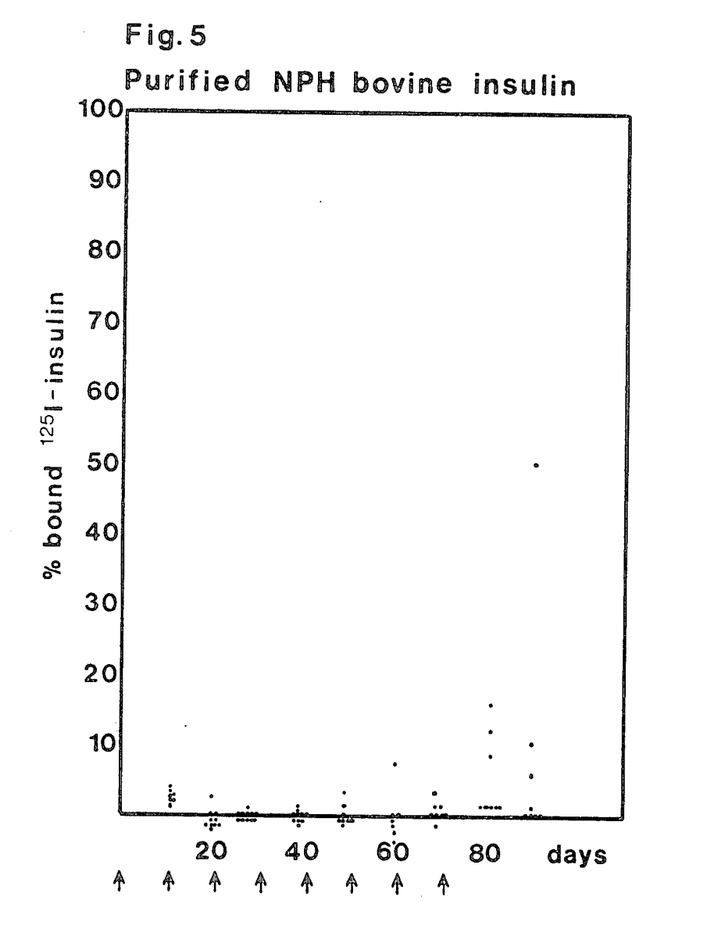
Figure 6:
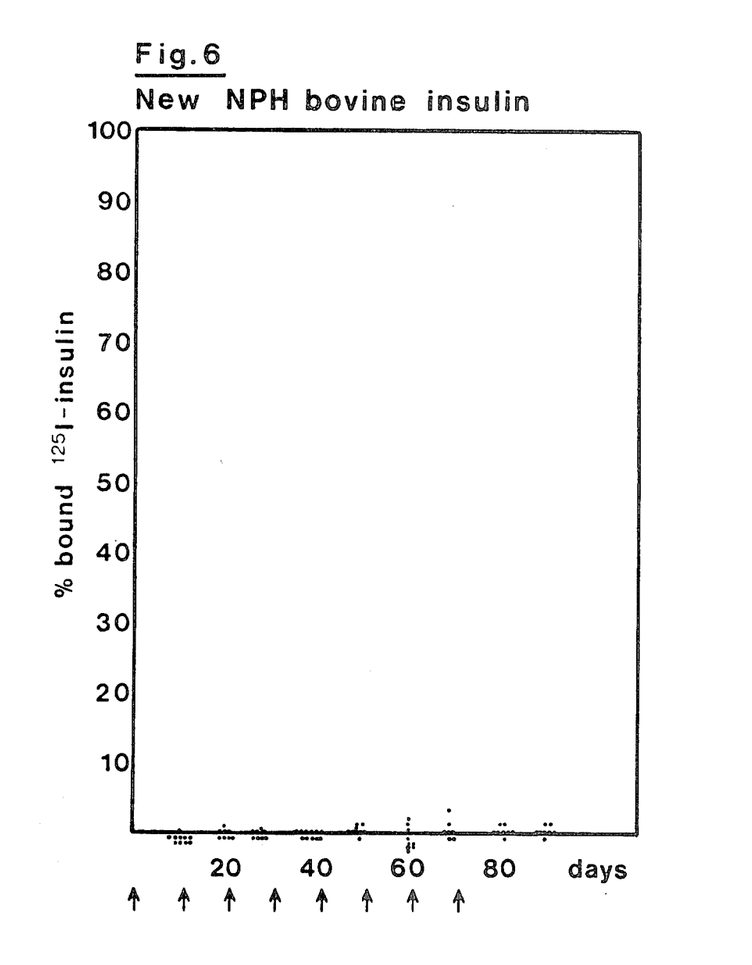

The obtained results are illustrated in FIGS. 4, 5 and 6.

It will be seen from the results that it was not possible to show any formation of antibody to the new NPH bovine insulin prepared according to the invention.

PEG Method for Antibody Determination

100 μl rabbit serum, 100 μl $^{125}$I-insulin, about 2 μU/ml, 100 μl insulin solution, 250 μU/ml and 700 μl phosphate buffer, 0.04 M pH 7.4 with 0.15 M NaCl and 0.5% human albumin was incubated for 48 hours at 4° C. 500 μl PEG 6000 was added, 360 g/l mixed on rotamixer and the sample was left to stand for one hour at 20° C.

After contrifuging for 10 minutes at 3000 r/min. the supernatant was decanted off and scrapped, $^{125}$I in precipitate was counted.

In each test is included a sample with an excess of guinea pig antibovine insulin, max.bonding, and a sample with rabbit serum from non-immunized rabbits, O-sample. The results were calculated as follows:

$$\%B = [(T-T_o)/(T_M-T_o)] \cdot 100$$

wherein
T=counting number for unknown,
$T_o$=counting number of O-sample,
$T_M$=counting number for max.bonding

LITERATURE (1) Hunter, R.: Standardization of the chloramine T method of protein iodination. Proc.Soc.Exp.Biol.Med. 133 (1970) 989.
(2) Desbuquois, B. & Aurbach, G. D.: Use of polyethylene glycol to separate free and antibody-bound peptide hormones in radioimmunoassays. J.Clim.Endocrinol. 33 (1971) 732.
(3) Gennaro, W. D. & Van Normone, J. D.: Quantitation of free, total and antibody-bound insulin in insulin-treated diabetics. Clin.Chem. 21/7 (1975) 873.
(4) Vinik, A. I., Jaffe, B. I., Seftel, H. C., Distiller, L. A. & Jackson, W. P. V.: Clinical aspects of monocomponent insulins in the treatment of diabetes. S.A. Medical Journal, April (1976) 587.

What we claim is:

1. In a process for producing a stable insulin preparation with protracted action, wherein insulin is purified to a state of reduced or no antigenicity and then is reacted with an organic base containing amino groups in an aqueous medium maintained at a pH of about 6 to about 9, and the insulin preparation is isolated, the improvement comprising utilizing for said reaction with said organic base a medium containing a protein depolymerizing or protein dissociating stabilizer to maintain said purified insulin in a dissolved monomeric or loosely aggregated form during said reaction, thereby producing a stable insulin preparation with protracted action and reduced or no antigencity.

2. A process according to claim 1, wherein the insulin is bovine insulin.

3. A process according to claim 1, wherein the medium is a buffered aqueous solution of urea.

4. A process according to claim 1, wherein the medium is a buffered aqueous solution containing a compound selected from the group consisting of a lower alkanol, dialkylformamide, acetamide, N-alkyl-acetamide and acetonitrile.

5. A process according to claim 1, wherein the medium is a buffered aqueous solution containing about 7 mol urea, and the reaction product is precipitated by dilution of the reaction mixture.

6. A process according to claim 1, wherein the organic base containing amino groups is a polypeptide or a cleavage product thereof.

7. A process according to claim 6, wherein the polypeptide is protamine.

8. A process according to claim 1, the improvement comprising the steps of subjecting insulin to a chromatographic purification using a buffered eluent containing a protein dissociating or protein depolymerizing stabilizer, isolating a fraction of the eluted product containing highly purified insulin, adding an aqueous solution of an organic base containing amino groups to said fraction, maintaining a pH of 6 to 9 and isolating the produced insulin preparation.

9. A process according to claim 8, wherein the insulin is bovine insulin.

10. A process according to claim 8, wherein the eluent is a buffered aqueous solution of urea.

11. A process according to claim 8, wherein the eluent is a buffered aqueous solution of a compound selected from the group consisting of a lower alkanol, dialkylformamide, acetamide, N-alkyl-acetamide and acetonitrile.

12. A process according to claim 8, wherein the eluent is a buffered aqueous solution containing about 7 mol urea, and the reaction product is precipitated by dilution of the reaction mixture.

13. A process according to claim 8, wherein the organic base containing amino groups is a polypeptide or a cleavage product thereof.

14. A process according to claim 13, wherein the polypeptide is protamine.

15. A process according to claim 8, wherein the eluent is an aqueous buffered solution containing 50–70% lower alkanol.

16. A process according to claim 15, wherein the lower alkanol is ethanol.

17. A process according to claim 8, wherein the insulin is also subjected to a gel filtration before the reaction with the organic base containing amino groups.

* * * * *